(12) United States Patent
Couture et al.

(10) Patent No.: US 9,277,894 B2
(45) Date of Patent: Mar. 8, 2016

(54) METHOD AND SYSTEM FOR INTEGRATED PATIENT TABLE DIGITAL X-RAY DOSIMETER

(71) Applicant: General Electric Company, Schenectady, NY (US)

(72) Inventors: Aaron Judy Couture, Schenectady, NY (US); Richard Larry Anderton, West Jordan, UT (US)

(73) Assignee: General Electric Company, Niskayuna, NY (US)

( * ) Notice: Subject to any disclaimer, the term of this patent is extended or adjusted under 35 U.S.C. 154(b) by 0 days.

(21) Appl. No.: 14/179,897

(22) Filed: Feb. 13, 2014

(65) Prior Publication Data

US 2015/0224343 A1 Aug. 13, 2015

(51) Int. Cl.
*G01T 1/02* (2006.01)
*G01T 5/06* (2006.01)
*A61B 6/04* (2006.01)
*G01T 1/20* (2006.01)

(52) U.S. Cl.
CPC .............. *A61B 6/04* (2013.01); *G01T 1/2018* (2013.01)

(58) Field of Classification Search
CPC .......... G01T 1/02; G01T 5/06; A61N 5/1071; A61N 5/1049
See application file for complete search history.

(56) References Cited

U.S. PATENT DOCUMENTS

| | | | |
|---|---|---|---|
| 5,262,649 A | 11/1993 | Antonuk et al. | |
| 5,661,310 A | 8/1997 | Jones | |
| 6,162,165 A | 12/2000 | Apple et al. | |
| 6,785,356 B2 | 8/2004 | Grass et al. | |
| 7,831,016 B2 | 11/2010 | Saoudi et al. | |
| 2006/0153341 A1* | 7/2006 | Guyonnet et al. | 378/207 |
| 2008/0023647 A1 | 1/2008 | Patel | |
| 2011/0036988 A1 | 2/2011 | Campbell et al. | |
| 2012/0106817 A1 | 5/2012 | Shih et al. | |
| 2013/0218001 A1* | 8/2013 | Uhlemann | 600/411 |

FOREIGN PATENT DOCUMENTS

JP 2012075666 A 4/2012

OTHER PUBLICATIONS

Balter et al., "Techniques to estimate radiation dose to skin during fluoroscopically guided proceduresα.", Skin Dose Measurements AAPM, pp. 1-10, Jul. 2002.
Miller et al.,"Mininnizing Radiation-induced Skin Injury in Interventional Radiology Procedures", Radiology, Sep. 13, 2002.
Miller et al.,"Radiation Doses in Interventional Radiology Procedures: The RAD-IR Study Part I: Overall Measures of Dose", Clinical Studies, pp. 711-727, Jun. 2003.
Gibson et al., "Technical White Paper:Monitoring and Tracking of Fluoroscopic Dose", CRCPD's H-31 Task Force for Monitoring Patient Dose during Fluoroscopy, pp. 1-15, Dec. 2010.
Petzel, "Fluoroscopy Safety", Department of Veterans Affairs VHA HANDBOOK 1105.04 Veterans Health Administration Transmittal Sheet Washington, DC 20420, pp. 1-26, Jul. 6, 2012.
International Search Report and Written Opinion for PCT Application No. PCT/US2015/015873, dated May 27, 2015, 11 pages.

* cited by examiner

*Primary Examiner* — David Porta
*Assistant Examiner* — Faye Boosalis
(74) *Attorney, Agent, or Firm* — Paul J. DiConza (57) ABSTRACT

A method of imaging a patient and an X-ray dosimetry system are provided. The X-ray dosimetry system includes a support platform configured to support an object to be imaged and a digital X-ray dosimeter mounted on a surface of the support platform, the X-ray dosimeter configured to receive incident radiation prior to the incident radiation having passed through the object to be imaged, the X-ray dosimeter comprising a thickness of less than about four millimeters.

12 Claims, 6 Drawing Sheets

METHOD AND SYSTEM FOR INTEGRATED PATIENT TABLE DIGITAL X-RAY DOSIMETER

BACKGROUND

This description relates to radiation detectors, and, more particularly, to a system and method for measuring peak skin dose of a patient directly on a patient examining table.

During fluoroscopic medical imaging procedures, injury to a patient and/or doctor may occur due to excessive exposure to radiation, and skin damage is a risk to both doctors as well as patients. To minimize a dose of radiation during such procedures, it is important to measure the peak dose delivered to the skin during fluoroscopic procedures. However, measurement of the peak skin dose has been challenging, and at least some known imaging systems do not include methods for tracking peak skin dose. Systems which include skin dose monitoring commonly employ calculation and estimation techniques in order to estimate peak skin dose. The estimate involves tracking the patient position and the X-ray tube output to track the peak skin dose delivered to the skin. Those systems do not typically include changes due to an examining table on which a patient is positioned or the patient geometry, for example, a size and a weight of the patient. The examining table may include operating, surgical, or other patient or workpiece support table.

Additionally, dose information for fluoroscopic procedures is also projected or modeled based on the position of the patient and the characteristics of the X-ray tube.

Commercial systems do not exist for the active measurement of peak skin dose across the full area of exposure. Dosimeters are available for personal exposure at a fixed point. Currently dosimeters are available for personal exposure at fixed points and a peak skin dose is estimated from the fixed point exposure, the known properties of the X-ray tube output, the known properties of the examining table on which the patient is positioned, and patient geometry. However, such dose calculations are merely estimates, which are not totalized in real-time.

BRIEF DESCRIPTION

In one embodiment, an X-ray dosimetry system includes a support platform configured to support an object to be imaged and a digital X-ray dosimeter mounted on a surface of the support platform. The X-ray dosimeter is configured to receive incident radiation prior to the incident radiation having passed through the object to be imaged and has a thickness of less than about four millimeters.

In another embodiment, a method of imaging a patient includes providing a patient support table including a digital X-ray dosimeter coupled to a surface of the patient support table. The digital X-ray dosimeter includes a flexible substrate layer, an electrode layer coupled to a conductive interconnect, a photodiode layer, a second electrode layer, and a flexible scintillator. The method further includes positioning a patient on the patient support table with a portion of the patient to be imaged located adjacent to the digital X-ray dosimeter, positioning an imaging detector on a side of the patient opposite from the patient support table, and displaying a peak skin dose to the patient with respect to a position of a body of the patient.

In yet another embodiment, a patient imaging system includes a support platform configured to support a human patient to be imaged and a digital radiation dosimeter configured to receive incident radiation prior to passing through the patient. The digital radiation dosimeter includes a substrate, an electrode electrically coupled to a conductive interconnect, a photodiode layer, and a scintillator layer and a thickness of less than about four millimeters. The system also includes an imaging radiation source positioned on a same side of the patient as the digital radiation detector and an imaging radiation detector positioned on a side opposite of the patient from the imaging radiation source and the digital radiation dosimeter. The digital radiation dosimeter is configured to measure a peak skin dose to the patient accumulated as a function of position of the patient and the imaging radiation source.

DRAWINGS

These and other features, aspects, and advantages of the present disclosure will become better understood when the following detailed description is read with reference to the accompanying drawings in which like characters represent like parts throughout the drawings, wherein.

Unless otherwise indicated, the drawings provided herein are meant to illustrate features of embodiments of the disclosure. These features are believed to be applicable in a wide variety of systems comprising one or more embodiments of the disclosure. As such, the drawings are not meant to include all conventional features known by those of ordinary skill in the art to be required for the practice of the embodiments disclosed herein.

DETAILED DESCRIPTION

The following detailed description illustrates embodiments of the disclosure by way of example and not by way of limitation. It is contemplated that the disclosure has general application to structural and methodical embodiments for the active measurement of peak skin dose of radiation to a patient during medical procedures. The measurement system is low cost, thin and flexible, and may be incorporated into an existing framework of surgical systems.

Embodiments of the disclosure describe incorporating a dose measurement device or dosimeter within the examining table that yields a peak skin dose accumulated as a function of position, with a size resolution of approximately 2-3 millimeter (mm) to approximately 1 centimeter (cm). The dosimeter is substantially transparent to the x-ray radiation, stopping only a few percent of the delivered dose. The dosimeter is placed in close proximity to the skin of a patient to accurately measure effects, such as, scattering which are influenced by patient placement, size and examining table geometry. As used herein, peak skin dose refers to a highest dose at any portion of a patient's skin during a procedure (integrated in time at a specific point on the skin).

The peak skin dose measurement device or dosimeter is part of an integrated dose detection system that works by placing a low cost, large area array of high x-ray transparency detectors onto a thin, flexible substrate. The x-ray detector pixels may be formed to be 2-3 mm in size and may be 1 cm or larger. The anode is formed by a conductive metal or conductive oxide. The photosensitive layer is an un-patterned thin film photodiode, which, in various embodiments, is formed of plasma-enhanced chemical vapor deposition (PECVD) amorphous silicon (a-Si) or a solution coated organic photodiode (OPD). A transparent conductive metal or oxide is deposited on top of the OPD absorber layer. The photodiode may alternately be sealed or encapsulated with a transparent material such as glass to form a protective environmental seal for the photodiode. A scintillator material is then attached or deposited onto the top electrode or barrier material. The scintillator thickness is just large enough to generate signal for the minimum detectable dose, which limits the absorption of x-rays in the detector. The scintillator may be a thin film deposited material or a plastic sheet with scintillator particles embedded in plastic binder, laminated using adhesive. Additionally, the scintillator may be directly printed onto the substrate or the photodiode.

The photodiode generates electrical current which increases as a function of x-ray flux during x-ray exposure. The electrical current is conducted thru metallic interconnects which are printed or patterned onto the flexible substrate. The conductors are either on the front (photodiode) side of the substrate and connected to the anode, or on the back side (opposite the photodiode) and electrically connected thru a via in the substrate. At the edge of the substrate, a series of TAB bond pads are provided for connection to external electronics, which are used to amplify and convert the current to digital information. The x-ray dosimeter sheet may be incorporated into existing examining tables either internally or laminated to the surface of the table. In some embodiments, the X-ray dosimeter is formed of a plurality of X-ray dosimeter subassemblies communicatively coupled to a dose measuring circuit that receives and processes signals representative of an amount of radiation received by the X-ray dosimeter subassemblies. In some embodiments, the X-ray dosimeter subassemblies are positioned in an abutting relationship adjacent to each other on the examining table and in other embodiments, the X-ray dosimeter subassemblies are positioned such that a gap is formed between adjacent subassemblies. Moreover, X-ray dosimeter subassemblies are permanently or semi-permanently affixed to the examining table, such as by being formed with the examining table or by using an adhesive. In other embodiments, X-ray dosimeter subassemblies are held in position by gravity or by static attraction.

As used herein, a radiation dosimeter differs from a radiation imaging detector in that a radiation dosimeter is used is an imaging system with an radiation imaging detector to determine peak skin dose with respect to a patient position and a position of a radiation imaging source. The radiation dosimeter is positioned on the same side of the patient as the radiation imaging source and receives the radiation prior to the radiation passing through a body of the patient. The radiation imaging detector receives the radiation after it has passed through the body of the patient. The radiation dosimeter is formed to be as radiation transparent as possible, while the radiation imaging detector is formed to absorb as much of the radiation reaching it as possible. Moreover, the pixel area of the radiation dosimeter is relatively larger than the pixel area of the radiation imaging detector making the resolution of the radiation imaging detector greater than the resolution of the radiation dosimeter.

The following description refers to the accompanying drawings, in which, in the absence of a contrary representation, the same numbers in different drawings represent similar elements.

Figure 1:
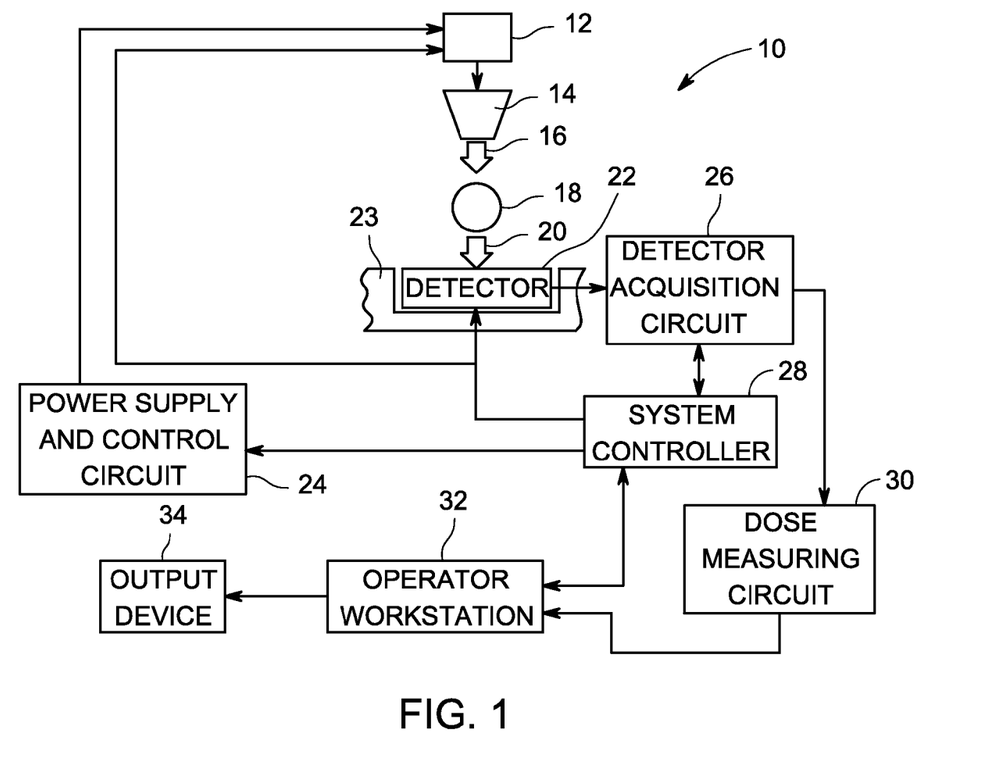
FIG. 1 is a schematic block diagram of an exemplary X-ray imaging system.

FIG. 1 is a schematic block diagram of an exemplary X-ray imaging system 10. In the exemplary embodiment, X-ray imaging system 10 is configured to acquire and process X-ray image data. X-ray imaging system 10 includes an X-ray source 12, a collimator 14, and a detector 22. Detector 22 is a fluoroscopic detector. Alternatively, detector 22 is a detector that enables the operation of X-ray imaging system 10 as described herein. In one embodiment, detector 22 is mounted on a support platform 23 by either coupling detector 22 to a surface of support platform 23 or embedded in a well formed in the surface of support platform 23. X-ray source 12 is positioned adjacent to collimator 14. In one embodiment, X-ray source 12 is a low-energy source and is employed in low energy imaging techniques, such as, but not limited to, fluoroscopic techniques. Collimator 14 facilitates a stream of X-ray radiation 16 emitted by X-ray source 12 to radiate towards a target 18, such as an industrial component or a human patient. A portion of X-ray radiation 16 is attenuated by target 18 and at least some attenuated radiation 20 impacts detector 22.

Detector 22 is based on scintillation, i.e., optical conversion, direct conversion, or on other techniques used in the generation of electrical signals based on incident radiation. For example, a scintillator-based detector converts X-ray photons incident on its surface to optical photons. These optical photons may then be converted to electrical signals by employing photosensor(s), e.g., photodiode(s). Conversely, a direct conversion detector directly generates electrical charges in response to incident X-ray photons. The electrical charges are stored and read out from storage capacitors. As described in detail below, these electrical signals, regardless of the conversion technique employed, are acquired and processed to construct an image of the features (e.g., anatomy) within target 18.

In the exemplary embodiment, X-ray source 12 is controlled by a power supply and control circuit 24 which supplies power and control signals for examination sequences. Moreover, detector 22 is coupled to a detector acquisition circuit 26, which is configured to receive electrical readout signals generated in detector 22. Detector acquisition circuit 26 may also execute various signal processing and filtration functions, such as, for initial adjustment of dynamic ranges and interleaving of digital signals.

In the exemplary embodiment, one or both of power supply/control circuit 24 and detector acquisition circuit 26 is responsive to signals from a system controller 28. System controller 28 includes signal processing circuitry, typically based upon a general purpose or application specific digital computer programmed to process signals according to one or more parameters. System controller 28 also includes memory circuitry for storing programs and routines executed by the computer, as well as configuration parameters and image data and interface circuits.

System 10 includes a dose measuring circuit 30 configured to receive acquired radiation data from detector acquisition circuit 26. Dose measuring circuit 30 is configured to process the acquired radiation data to a dose received at detector 22. In various embodiments, detector 22 receives stream of X-ray radiation 16 before it passes through target 18. In these embodiments, X-ray source 12 and collimator 14 are located on a side opposite of detector 22 from target 18. For example, in FIG. 1, X-ray source 12 and collimator 14 could be positioned below support platform 23 and configured to direct stream of X-ray radiation 16 upward through support platform 23, detector 22, and into target 18.

An operator workstation 32 is communicatively coupled to system controller 28 and/or dose measuring circuit 30 to allow an operator to initiate and configure X-ray imaging of target 18 and to view images generated from X-rays that impinge detector 22. For example, system controller 28 is in communication with operator workstation 32 so that an operator, via one or more input devices associated with operator workstation 32, may provide instructions or commands to system controller 28.

Similarly, dose measuring circuit 30 is in communication with operator workstation 32 such that operator workstation 32 receives and displays the output of dose measuring circuit 30 on an output device 34, such as a display or printer. Output device 34 may include standard or special purpose computer monitors and associated processing circuitry. In general, displays, printers, operator workstations, and similar devices supplied within system 10 may be local to the data acquisition components or may be remote from these components, such as elsewhere within an institution or hospital or in an entirely different location. Output devices and operator workstations that are remote from the data acquisition components may be operatively coupled to the image acquisition system via one or more configurable networks, such as the Internet or virtual private networks. Though system controller 28, dose measuring circuit 30, and operator workstation 32 are shown distinct from one another in FIG. 1, these components may actually be embodied in a single processor-based computing system. Alternatively, some or all of these components may be present in distinct processor-based computing systems configured to communicate with one another. For example, dose measuring circuit 30 may be a component of a distinct reconstruction and viewing workstation.

Figure 2:
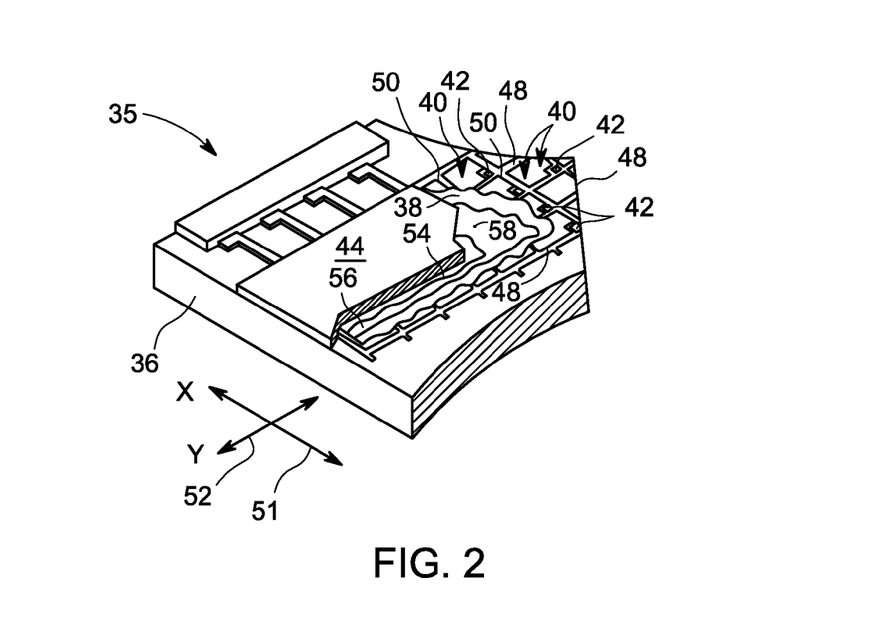
FIG. 2 is a perspective cut-away view of a physical arrangement of the components of an exemplary scintillation-based detector suitable for use with the X-ray imaging system shown in FIG. 1.

FIG. 2 is a perspective cut-away view of a physical arrangement of the components of an exemplary scintillation-based detector 35 suitable for use as detector 22 depicted in FIG. 1. Detector 35 includes a flexible substrate 36 upon which one or more components are deposited. For example, in the present embodiment, detector 35 includes a continuous photosensor element 38, transistors 42, such as, but not limited to amorphous Silicon (a-Si), thin-film transistors (TFTs), scintillator 44, data readout lines 48, scan lines 50, a conductive layer 54, and a dielectric layer 56 deposited with respect to substrate 36. The components of detector 35 are composed of metallic, dielectric, organic, and/or inorganic materials, and are fabricated with respect to substrate 36 using various material deposition and removal techniques. Some examples of deposition techniques include, for example, chemical vapor deposition, physical vapor deposition, electrochemical deposition, stamping, printing, sputtering, and/or any other suitable deposition technique. Some examples of material removal techniques include lithography, etching, such as, but not limited to dry etching, wet etching, laser etching, sputtering, and/or any other suitable material removal techniques.

Detector 35 includes an array of pixel areas 40 on flexible substrate 36. Each of pixel areas 40 includes transistors 42 operatively coupled to respective data readout lines 48, scan lines 50, and photosensor 38. In the present embodiment, transistors 42 are arranged in a two dimensional array having rows extending along an x-axis 51 and columns extending along a y-axis 52, or vice versa. In some embodiments, transistors 42 are arranged in other configurations. For example, in some embodiments, transistors 42 are arranged in a honeycomb pattern. A spatial density of transistors 42 determines a quantity of pixel areas 40 or pixels in the array, the physical dimensions of the array, as well as the pixel density or resolution of detector 35.

Each of data readout lines 48 is in electrical communication with an output of a respective transistor 42. For example, each of data readout lines 48 is associated with a row or column of transistors 42, and the output (e.g., source or drain) of each transistor 42 in the row or column is in electrical communication with the same data readout line 48 such that there is one data readout line per row or column. Data readout lines 48 are susceptible to interference, such as electronic noise from a surrounding environment, which affects data signals being transmitted on data readout lines 48. Data readout lines 48 are formed of a conductive material, such as a metal, and are configured to facilitate transmission of electrical signals, corresponding to incident X-rays, to image processing circuitry, for example, within dose measuring circuit 30.

Scan lines 50 are in electrical communication with inputs (e.g., gates) of transistors 42. For example, each of scan lines 50 is associated with a row or column of transistors 42 and the input of each of transistors 42 in the same row or column is in electrical communication with one of scan lines 50. Electrical signals transmitted on scan lines 50 are used to control transistors 42 to output data on the transistor's output such that each transistor 42 connected to one of scans lines 50 are configured to output data concurrently and data from each transistor 42 connected to one of scan lines 50 flows through data readout lines 48 in parallel. In various embodiments, scan lines 50 and data readout lines 48 extend perpendicularly to one another to form a grid. Scan lines 50 are formed of a conductive material, such as a metal, and are configured to facilitate transmission of electrical signals from a controller (e.g., system controller 28) to an input of transistors 42.

Continuous photosensor 38 is deposited over transistors 42, data readout lines 48, and/or scan lines 50. Photosensor 38 is formed from one or more photoelectric materials, such as one or more organic (i.e., carbon-based) and/or inorganic (i.e., non-carbon-based) materials that that convert light into electric current. In the present embodiment, the photoelectric material extends continuously as a unitary structure over the array of transistors 42, data readout lines 48, and scan lines 50 such that the photoelectric material of photosensor 38 substantially overlays and/or covers pixel areas 40. By using a continuous unpatterned photoelectric material that is disposed over the transistor array, the density of transistors 42 in the array, and therefore, the pixel density of the detector, is increased as compared to patterned photosensors and/or a complexity of detector fabrication is reduced.

Electrodes, such as, but not limited to, electrical contacts of photosensor 38 define anode(s) and cathode(s) of photosensor 38 and are formed of a conductive material, such as, for example, indium tin oxide (ITO). For example, photosensor 38 includes electrodes disposed on a first side of photosensor 38 for electrically coupling the first side of photosensor 38 to transistors 42 and includes one or more electrodes disposed on a second opposing side of photosensor 38 for electrically coupling the second side of photosensor 38 to a bias voltage or vice versa. The electrodes of photosensor 38 form the anode(s) or cathode(s) of photosensor 38.

A dielectric layer 56 is disposed over continuous photosensor 38 and a conductive layer 54 is disposed on dielectric layer 56. Dielectric layer 56 includes vias 58 to electrically couple conductive layer 54 to the electrode(s) of photosensor 38 to allow a common bias voltage to be applied at each pixel area 40 of detector 35.

Scintillator 44 is disposed over conductive layer 54 and generates the optical photons when exposed to X-rays. The optical photons emitted by scintillator 44 are detected by photosensor 38, which converts the optical photons to an electrical charge that is output through transistors 42 to data readout lines 48. Scintillator 44 may be a thin film deposited material or a plastic sheet with scintillator particle embedded in plastic binder, laminated using adhesive. Additionally, in various embodiments, scintillator 44 is directly printed onto substrate 36 or the photosensor 38.

Figure 3:
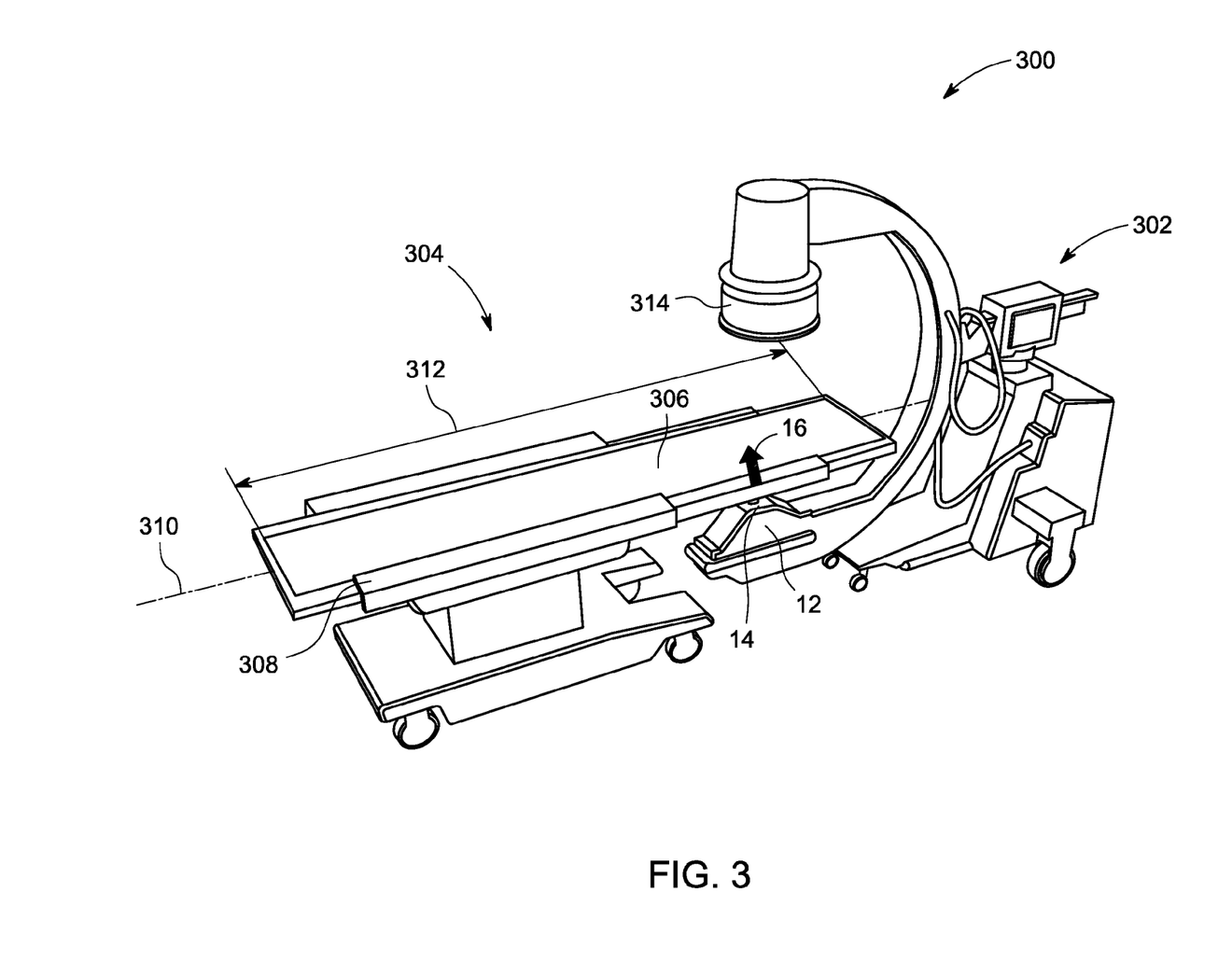
FIG. 3 is a perspective view of an exemplary C-arm X-ray fluoroscopy system.

FIG. 3 is a perspective view of an exemplary C-arm X-ray fluoroscopy system 300. In the exemplary embodiment, a C-arm assembly 302 is used with a patient examining table assembly 304 to perform medical operations on a patient (not shown in FIG. 3). A large-format digital X-ray dosimeter, also referred to as a dosimetry detector 306 is positioned on or within a support platform 308 of patient examining table assembly 304. Dosimetry detector 306 extends along a longitudinal axis 310 of patient examining table assembly 304 for a predetermined distance 312. In one embodiment, distance 312 is equal to a length of patient examining table assembly 304. In various embodiments, distance 312 is less than the length of patient examining table assembly 304. For example, in one embodiment, distance 312 is less than a length of a volume of examining table below patient examining table assembly 304 such that dosimetry detector 306 and support platform 308 receive stream of X-ray radiation 16 prior to a patient (not shown in FIG. 3) receiving stream of X-ray radiation 16 and before a portion of stream of X-ray radiation 16 that has passed through the patient reaches an imaging detector 314. In one embodiment, dosimetry detector 306 is sized to cover greater than ten per-cent of a surface area of patient examining table assembly 304. In another embodiment, dosimetry detector 306 is sized to cover greater than fifty per-cent of a surface area of patient examining table assembly 304. In some embodiments, patient examining table assembly 304 includes a depression 315 formed in the surface of patient examining table assembly 304 where depression 315 is sized complementary to a size and thickness of dosimetry detector 306. Dosimetry detector 306 is adhesively coupled to the surface of patient examining table assembly 304 or is formed integrally with the surface of patient examining table assembly 304. In various embodiments, patient examining table assembly 304 is embodied in a cardiology table, a surgical table, or an angiography table.

Figure 4:
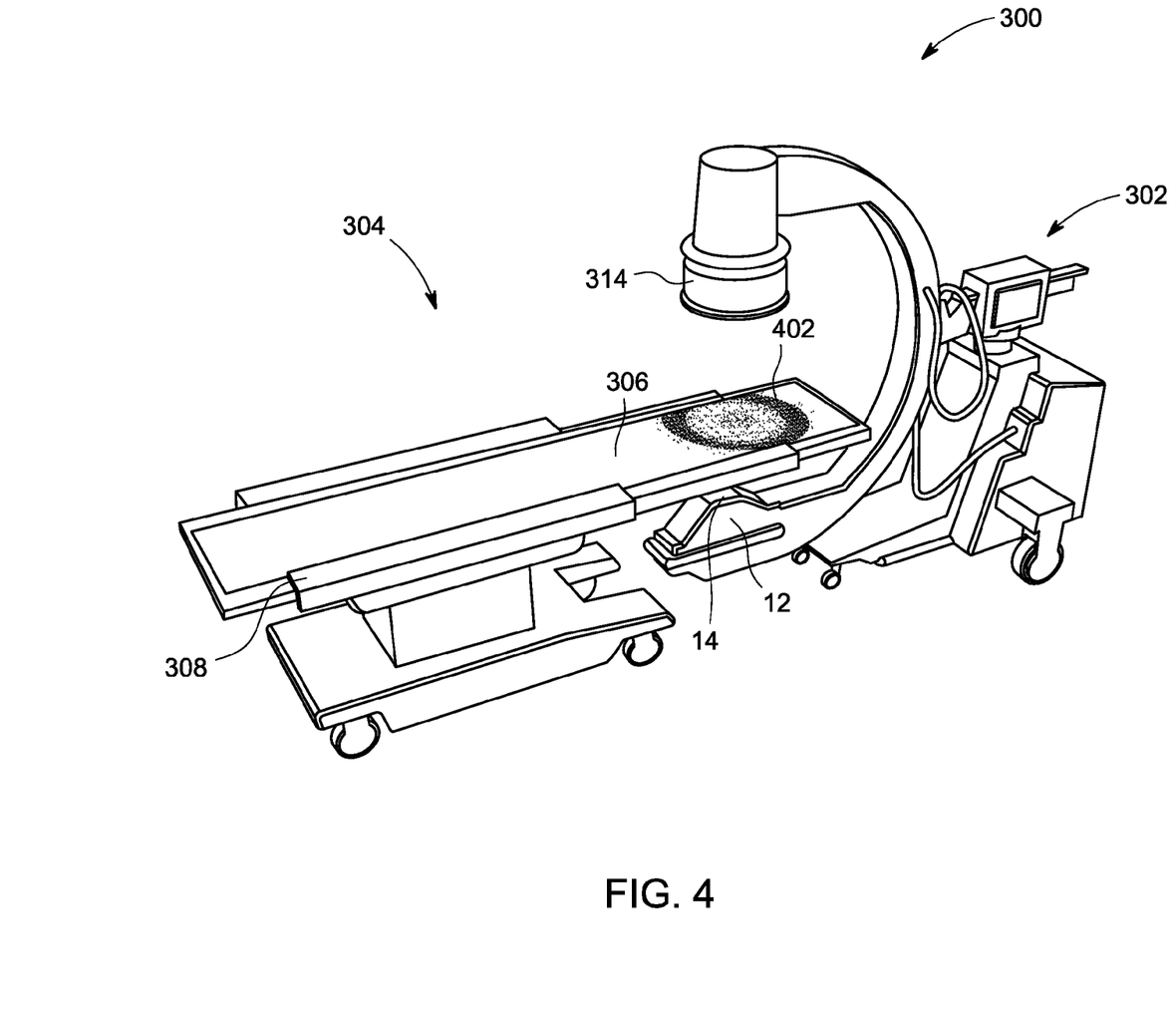
FIG. 4 is a perspective view of the C-arm X-ray fluoroscopy system shown in FIG. 3 including an X-ray flux field illustrated thereon.

FIG. 4 is a perspective view of C-arm X-ray fluoroscopy system 300. In the exemplary embodiment, a flux field 402 of X-ray radiation being detected by dosimetry detector 306 is visually depicted on dosimetry detector 306 where variations in the shading of the depiction are indications of the variation in flux field intensity. The visual depiction of flux field 402 illustrates the difficulty of using a point dosimeter that only measures the flux at a particular point. An intensity of flux field 402 is shown to vary widely over a relatively small area. A small displacement of the point dosimeter from a position assumed in an estimation calculation results in a large error in the peak skin dose calculation.

Figure 5:
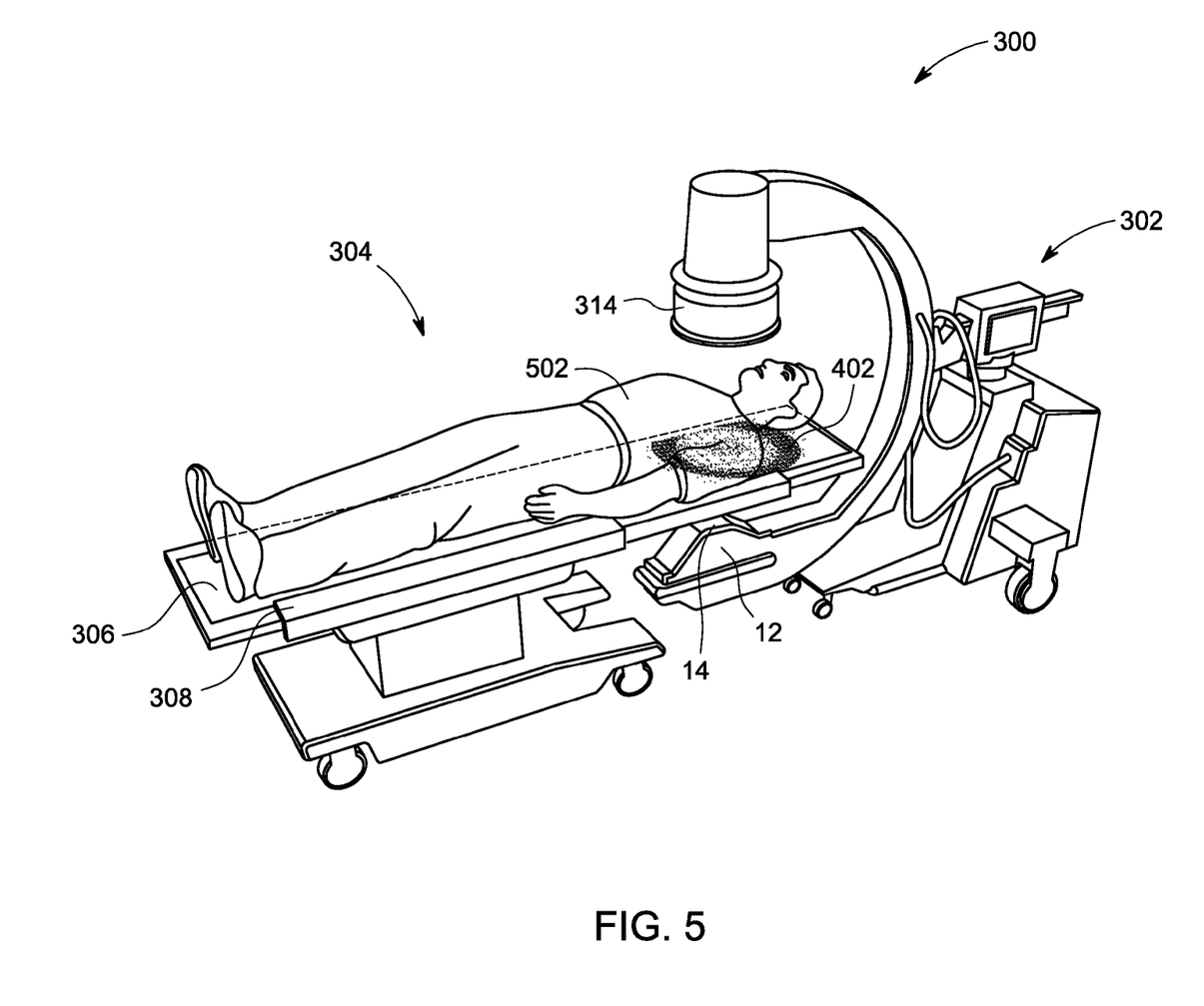
FIG. 5 is another perspective view of the C-arm X-ray fluoroscopy system shown in FIGS. 3 and 4 including a patient positioned thereon.

FIG. 5 is a perspective view of C-arm X-ray fluoroscopy system 300. In the exemplary embodiment, flux field 402 of X-ray radiation being detected by dosimetry detector 306 is visually depicted on dosimetry detector 306 while a patient 502 is positioned on examining table assembly 304. The visual depiction of flux field 402 illustrates the difficulty of using a point dosimeter that only measures the flux at a particular point. An intensity of flux field 402 is shown to vary widely over a relatively small area and over a portion of patient 502 that is subject to an examination or procedure using positioning of examination implements within patient 502 while observing the placement using fluoroscopy system 300. A small displacement of the point dosimeter from a position assumed in an estimation calculation results in a large error in the peak skin dose calculation for the patient, the doctor, and other medical personnel assisting in the procedure.

Figure 6:
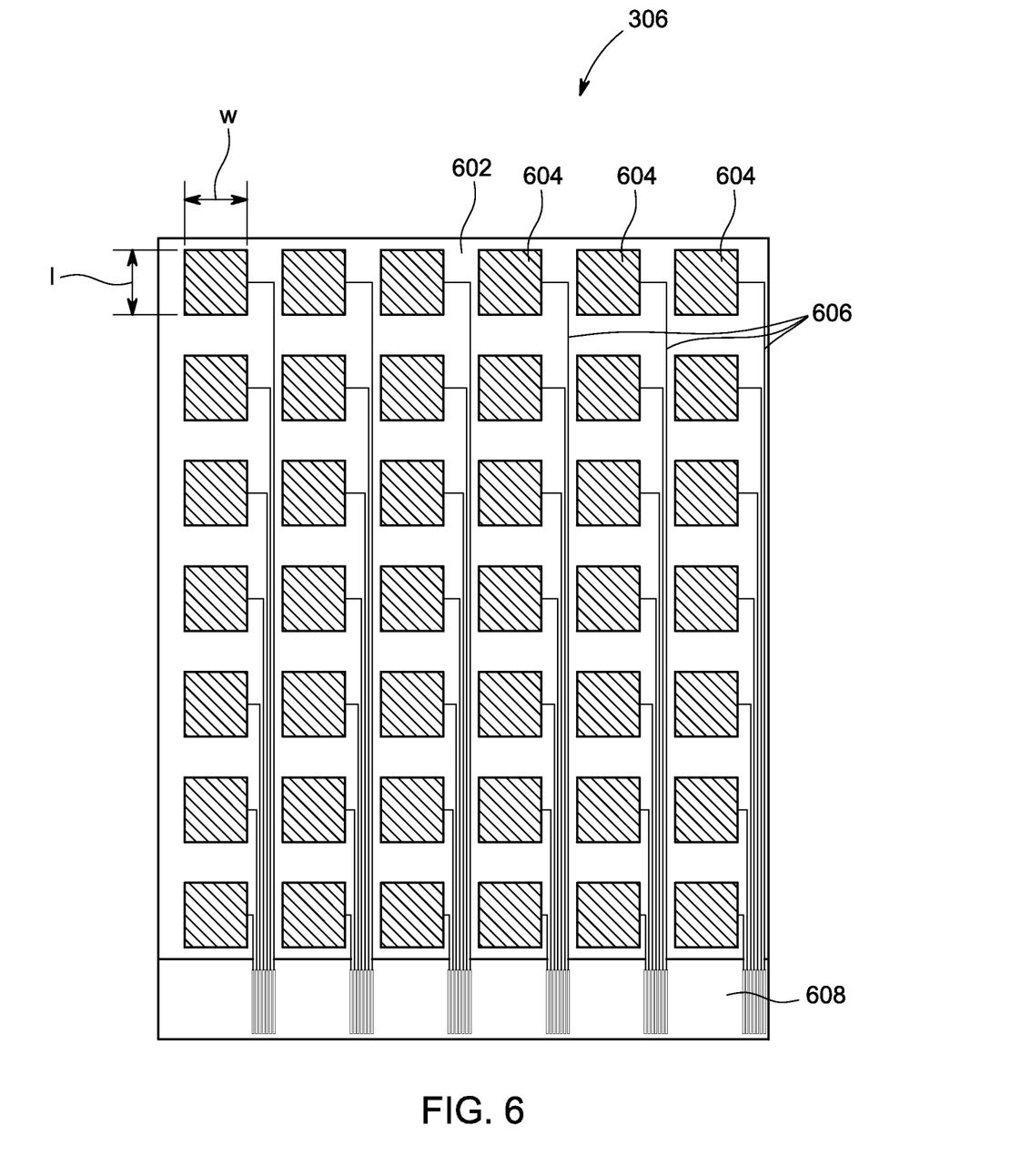
FIG. 6 is a plan view of a layout of pixels of dosimetry detector shown in FIG. 3.

FIG. 6 is a plan view of a layout of pixels of dosimetry detector 306. In the exemplary embodiment, dosimetry detector 306 is used for a real-time active measurement of peak skin dose to a patient during medical procedures. As used herein, real-time refers to outcomes occurring at a substantially short period after a change in the inputs affecting the outcome, for example, events occurring in real-time occur without substantial intentional delay.

Dosimetry detector 306 includes a substrate 602 on which layers of pixels 604 of X-ray radiation detector structure are formed as described below. In the exemplary embodiment, pixels 604 are formed in columns and rows spaced approximately uniformly with respect to each other. An interconnect 606 couples each pixel to read-out electronics using a tape-automated bonding (TAB) connection 608. Each of pixels 604 are sized to a predetermined length l and width w. In the exemplary embodiment, l and w are selected to be approximately 2.0 millimeters (mm) In other embodiments, l and w are selected to be approximately 1 centimeter (cm). In various embodiments, l and w are selected to be unequal distances. For example, a pixel resolution of dosimetry detector 306 may vary across the length or width of dosimetry detector 306. A particular patient examining table assembly 304 may be associated with a particular application, such as, but, not limited to heart applications. Because a major portion of the radiation dose is expected in the vicinity proximate the placement of the heart over a certain area of patient examining table assembly 304, the pixel resolution in that area may be selected to be greater in that area (i.e., l and/or w are relatively smaller values). Because pixels 604 are sized so large, each of pixels 604 is addressed individually and multi-plexing of the signals from pixels 604 is not used. Also because pixels 604 are so large, dosimetry detector 306 is not particularly suitable for digital X-ray imaging. This is one differentiating factor between an imaging digital X-ray detector, such as detector 35 (shown in FIG. 2) and dosimetry detector 306. The large size of pixels 604 also permits dosimetry detector 306 to be fabricated at relatively low cost. Accordingly, dosimetry detector 306 is low cost, thin and flexible, and is incorporated into an existing framework of surgical systems.

Figure 7:
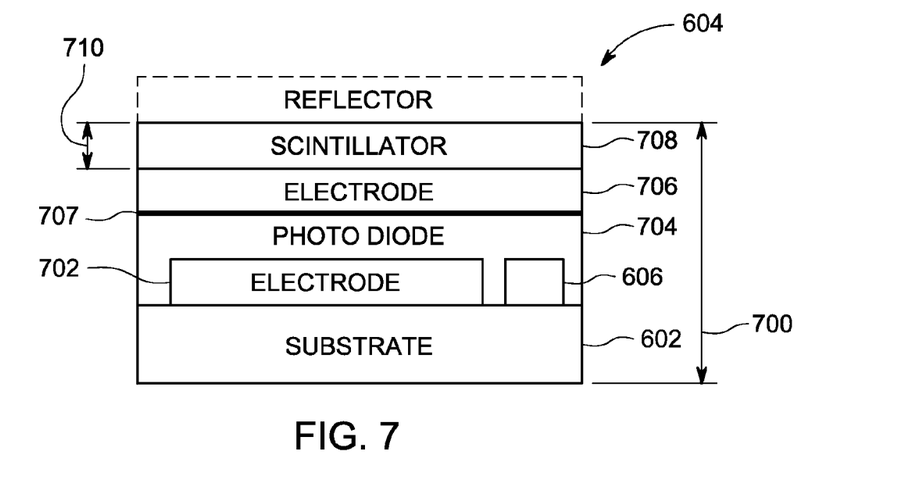
FIG. 7 is a side elevation view of the pixel shown in FIG. 6 using a top-side interconnect.
Figure 8:
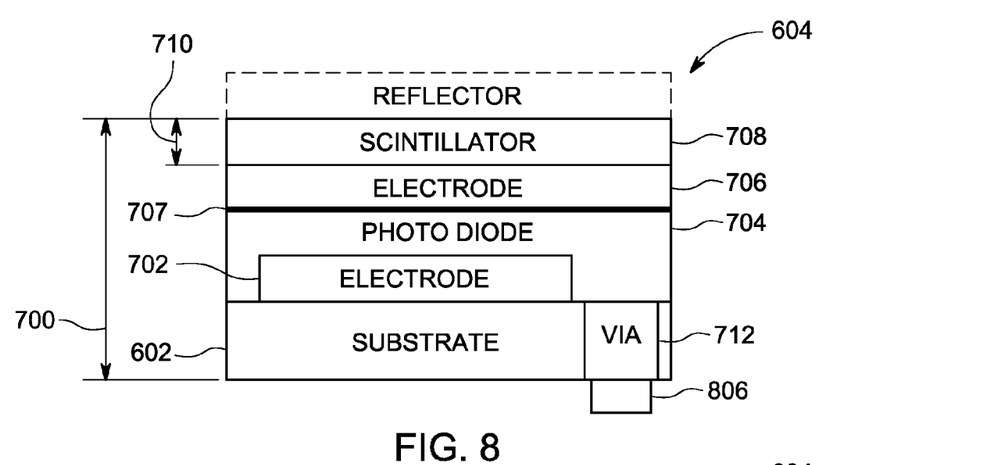
FIG. 8 is a side elevation view of the pixel shown in FIG. 6 using a bottom-side interconnect.

FIG. 7 is a side elevation view of pixel 604 using a top-side interconnect. FIG. 8 is a side elevation view of pixel 604 using a bottom-side interconnect. In the exemplary embodiment, pixel 604 is formed on flexible substrate 602. A total thickness 700 of pixel 604 and substrate 602 is approximately one-eighth inch (3.175 millimeters). An anode layer 702, which is formed by a conductive metal or conductive oxide and an interconnect 606 are printed on substrate 602. A photodiode layer 704 is an un-patterned thin film photodiode, which, in various embodiments, is formed of plasma-enhanced chemical vapor deposition (PECVD) amorphous silicon (a-Si) or a solution coated organic photodiode (OPD). A transparent conductive metal or oxide electrode layer 706 is deposited over photodiode layer 704. In various embodiments, photodiode layer 704 is sealed or encapsulated with a transparent barrier layer 707, such as, but not limited to, glass to form a protective environmental seal for photodiode layer 704. A scintillator layer 708 is then attached or deposited onto electrode layer 706 or barrier layer 707. A thickness 710 of scintillator layer 708 is selected to be just large enough to generate a signal for a minimum detectable dose, which limits the absorption of x-rays in the detector. In the exemplary embodiment, a TFT array is not needed because an image is not being stored. Scintillator layer 708 may be a thin film deposited material or a plastic sheet with scintillator particle embedded in plastic binder, laminated using adhesive.

Because pixels 604 are relatively large, as compared to, for example, imaging detector pixels, each individual pixel has its own data channel that it feeds out information to. Consequently, because the number data channels to read out is relatively small, the data channels do not need to be multiplexed, further making the electronic read-out circuitry simpler. Pixels 604 are formed differently than for an imaging detector because when forming an image, it is desirable to stop or count as many X-rays as possible and convert that information into light. In the exemplary embodiment, it is desirable to form scintillator layer 708 just thick enough to generate an X-ray signal by stopping as few X-rays as possible to generate the signal. Scintillator layer 708 is tuned to have a coefficient of transmission for X-rays that is less than or equal to a coefficient of transmission for X-rays of support platform 308 (shown in FIGS. 3 and 5). In this way a portion of the total X-ray flux passing through support platform 308 and detector 306 (shown in FIGS. 3 and 5) is sufficient for performance of the medical imaging being done on the patient. Photodiode layer 704 generates electrical current which increases as a function of X-ray flux during X-ray exposure. The electrical current is conducted through metallic interconnects 606, which are printed or patterned onto flexible substrate 602, as shown in FIG. 7 or through metallic interconnects 806 as shown in FIG. 8. Conductors (not shown in FIGS. 7 and 8) are either on the top (photodiode) side of substrate 602 (as shown in FIG. 7) and connected to an anode, or on the bottom side (opposite the photodiode) and electrically connected thru a via 712 in substrate 602 (shown in FIG. 8). At the edge of substrate 602, a series of TAB bond pad connections 608 (shown in FIG. 6) are provided for connection to data acquisition circuit 26 (shown in FIG. 1), which are used to amplify and convert the current to digital information. Dosimetry detector 306 is incorporated into existing examining tables, such as, but, not limited to, support platform 308 either internally or laminated to the surface of support platform 308.

Figure 9:
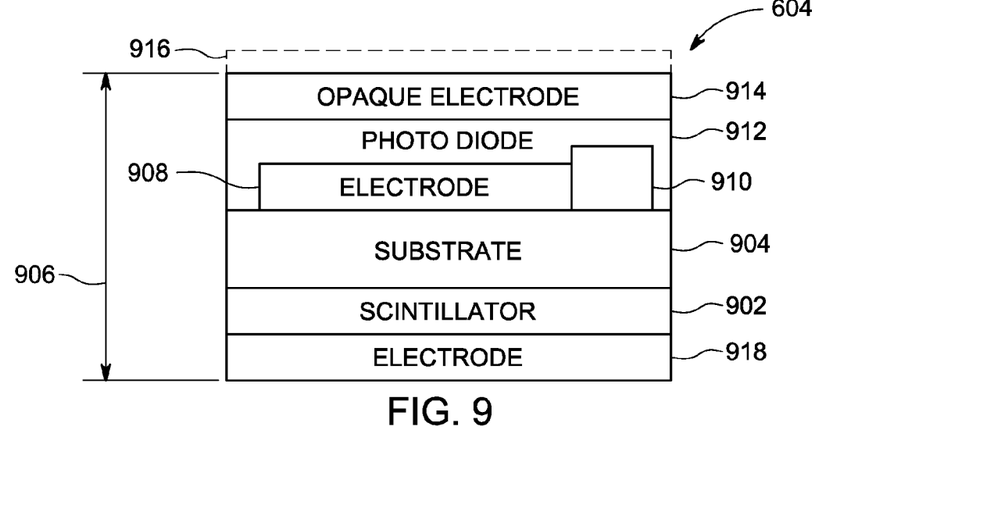
FIG. 9 is a side elevation view of another embodiment of the pixel shown in FIG. 6 using a back-side scintillator.

FIG. 9 is a side elevation view of another embodiment of pixel 604 using a back-side scintillator 902. In the exemplary embodiment, pixel 604 is formed on a substrate 904. A total thickness 906 of pixel 604 is approximately one-eighth inch (3.175 millimeters). An anode layer 908, which is formed by a conductive metal or conductive oxide and an interconnect 910 are printed on substrate 904. A photodiode layer 912 is an un-patterned thin film photodiode, which, in various embodiments, is formed of plasma-enhanced chemical vapor deposition (PECVD), amorphous silicon (a-Si), or a solution coated organic photodiode (OPD). An opaque and reflective conductive metal or oxide electrode layer 914 is deposited over photodiode layer 912. An optional barrier layer 916, such as, but not limited to, glass forms a protective environmental seal for electrode layer 914. Scintillator layer 902 is attached or deposited onto substrate 904 on a side opposite to that of photodiode layer 912, electrode layer 914, and optional barrier layer 916. A reflector layer 918 is deposited over scintillator layer 902. A thickness 710 of scintillator layer 708 is selected to be just large enough to generate a signal from photodiode layer 912 for a minimum detectable dose, which limits the absorption of x-rays in the detector.

Embodiments of this disclosure describe incorporating a peak skin dose measurement device or dosimeter within the examining table that yields peak skin dose accumulated as a function of position, with a size resolution of approximately 2-3 millimeter (mm) to approximately 1 centimeter (cm). The dosimeter is substantially transparent to the x-ray radiation, stopping only a few percent of the delivered dose. The dosimeter is placed in close proximity to the skin of a patient to accurately measure effects, such as, scattering which is influenced by patient placement, size and examining table geometry. The dose measurement device or dosimeter is part of an integrated dose detection system that works by placing a low cost, large area array of high x-ray transparency detectors onto a thin, flexible substrate. The x-ray detector pixels are formed to be 2.0-3.0 mm in size and 1.0 cm or larger.

It will be appreciated that the above embodiments that have been described in particular detail are merely example or possible embodiments, and that there are many other combinations, additions, or alternatives that are included.

Also, the particular naming of the components, capitalization of terms, the attributes, data structures, or any other programming or structural aspect is not mandatory or significant, and the mechanisms that implement the disclosure or its features may have different names, formats, or protocols. Further, the system may be implemented via a combination of hardware and software, as described, or entirely in hardware elements. Also, the particular division of functionality between the various system components described herein is merely one example, and not mandatory; functions performed by a single system component may instead be performed by multiple components, and functions performed by multiple components may instead performed by a single component.

The singular forms "a", "an", and "the" include plural references unless the context clearly dictates otherwise.

Some portions of above description present features in terms of algorithms and symbolic representations of operations on information. These algorithmic descriptions and representations are used by those skilled in the data processing arts to most effectively convey the substance of their work to others skilled in the art. These operations, while described functionally or logically, are understood to be implemented by computer programs. Furthermore, it has also proven convenient at times, to refer to these arrangements of operations as modules or by functional names, without loss of generality.

Unless specifically stated otherwise as apparent from the above discussion, it is appreciated that throughout the description, discussions utilizing terms such as "processing" or "computing" or "calculating" or "determining" or "displaying" or "providing" or the like, refer to the action and processes of a computer system, or similar electronic computing device, that manipulates and transforms data represented as physical (electronic) quantities within the computer system memories or registers or other such information storage, transmission or display devices.

Based on the foregoing specification, the above-discussed embodiments of the disclosure are implemented using computer programming or engineering techniques including computer software, firmware, hardware or any combination or subset thereof. Any such resulting program, having computer-readable and/or computer-executable instructions, are embodied or provided within one or more computer-readable media, thereby making a computer program product, i.e., an article of manufacture, according to the discussed embodiments of the disclosure. The computer readable media may be, for instance, a fixed (hard) drive, diskette, optical disk, magnetic tape, semiconductor memory such as read-only memory (ROM) or flash memory, etc., or any transmitting/receiving medium such as the Internet or other communication network or link. The article of manufacture containing the computer code is made and/or is used by executing the instructions directly from one medium, by copying the code from one medium to another medium, or by transmitting the code over a network.

Approximating language, as used herein throughout the specification and claims, are applied to modify any quantitative representation that could permissibly vary without resulting in a change in the basic function to which it is related. Accordingly, a value modified by a term or terms, such as "about" and "substantially", are not to be limited to the precise value specified. In at least some instances, the approximating language may correspond to the precision of an instrument for measuring the value. Here, and throughout the specification and claims, range limitations may be combined and/or interchanged, such ranges are identified and include all the sub-ranges contained therein unless context or language indicates otherwise.

While the disclosure has been described in terms of various specific embodiments, it will be recognized that the disclosure may be practiced with modification within the spirit and scope of the claims.

The above-described embodiments of a system and method of radiation dosimetry provides a cost-effective and reliable means for measuring a peak skin dose of radiation delivered to a patient and/or medical professional during a procedure where radiological imaging is also performed. As a result, the system and method described herein facilitate monitoring and reducing dose to patients and medical professionals in a cost-effective and reliable manner.

This written description uses examples to describe the disclosure, including the best mode, and also to enable any person skilled in the art to practice the disclosure, including making and using any devices or systems and performing any incorporated methods. The patentable scope of the disclosure is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A patient imaging system comprising:
    a support platform configured to support a human patient to be imaged;
    a digital X-ray dosimeter configured to receive incident radiation prior to passing through the patient, said digital radiation dosimeter comprising a substrate, an electrode electrically coupled to a conductive interconnect, a photodiode layer, and a scintillator layer, said digital radiation dosimeter comprising a thickness of less than about four millimeters;
    an X-ray source positioned on a same side of the support platform as said digital radiation dosimeter; and
    an imaging X-ray detector positioned on a side opposite of the support platform from said X-ray source and said digital X-ray dosimeter, where
    said digital X-ray dosimeter is configured to measure a peak skin radiation dose to the patient accumulated as a function of position of the patient and said X-ray source.

2. The system of claim 1, wherein a pixel resolution of said digital X-ray dosimeter varies across at least one of a length and a width of said digital X-ray dosimeter.

3. The system of claim 1, wherein a pixel resolution of aid digital X-ray dosimeter is about one centimeter.

4. The system of claim 1, wherein said digital X-ray dosimeter is sized to cover greater than ten per-cent of a surface area of said support platform.

5. The system of claim 1, wherein said digital X-ray dosimeter is sized to cover greater than fifty per-cent of a surface area of said support platform.

6. The system of claim 1, wherein said digital X-ray dosimeter is adhesively coupled to said surface of said support platform.

7. The system of claim 1, wherein said digital X-ray dosimeter is formed integrally with said surface of said support platform.

8. The system of claim 1, wherein said digital X-ray dosimeter comprises a plurality of layers including a substrate layer, an electrode layer coupled to a conductive interconnect, a photodiode layer, a second electrode layer, a barrier layer, and a scintillator layer.

9. The system of claim 1, wherein said support platform comprises at least one of a cardiology table, a surgical table, and an angiography table.

10. The system of claim 1, wherein said support platform forms said substrate.

11. The system of claim 1, wherein a pixel resolution of said digital X-ray dosimeter is about two millimeters.

12. The system of claim 1, wherein said digital X-ray dosimeter is sized to cover greater than twenty per-cent of a surface area of said support platform.

* * * * *